United States Patent [19]
Fenn

[11] Patent Number: 5,737,384
[45] Date of Patent: Apr. 7, 1998

[54] X-RAY NEEDLE PROVIDING HEATING WITH MICROWAVE ENERGY

[75] Inventor: Alan J. Fenn, Wayland, Mass.

[73] Assignee: Massachusetts Institute of Technology, Cambridge, Mass.

[21] Appl. No.: 725,728

[22] Filed: Oct. 4, 1996

[51] Int. Cl.⁶ .................................................. A61N 5/10
[52] U.S. Cl. ........................ 378/65; 378/121; 607/101
[58] Field of Search ........................ 378/65, 121, 200; 607/101

[56] References Cited

U.S. PATENT DOCUMENTS 5,165,093  11/1992  Miller et al. ............................ 378/130

*Primary Examiner*—Craig E. Church
*Attorney, Agent, or Firm*—Ellsworth R. Roston; Fulwider Patton Lee & Utecht, LLP

[57] ABSTRACT

Electrons moving in a first direction are concentrated (e.g. magnetically) in a beam within a first tube. A converter converts the electrons to x-rays for movement to a particular position (e.g. tumor) in a patient. A fluid (e.g. water) flowing past the converter through a second tube co-axial with the first tube cools the converter. Microwave energy passes in the first direction through a third tube co-axial with the first tube. The third tube is open at the end near the converter so that the microwave energy will pass to the particular position in the patient. A second fluid (e.g. air) passing through a fourth tube coaxial with the first tube cools the tissue in direct contact with the x-ray needle. The second, third and fourth tubes may respectively have diameters of approximately 2, 3 and 4 millimeters. The microwave energy may pass into the third tube from a fifth tube transverse to the third tube. The microwave energy impedance may be approximately 50 Ω at the fifth tube input and approximately 5 Ω at the third tube input. The fifth tube is constructed to match the 50 Ω and 5 Ω impedances. A first portion of the microwave energy introduced to the third tube flows in the first direction through the third tube coaxially with the electron beam. A second portion of the microwave energy flows in a direction opposite to the first direction, is reflected by a short circuit and then flows in the first direction in phase with the first energy portion.

25 Claims, 2 Drawing Sheets

X-RAY NEEDLE PROVIDING HEATING WITH MICROWAVE ENERGY

This invention relates to apparatus for, and methods of treating tumors. More particularly, the invention relates to apparatus for, and methods of, applying different types of energy to a tumor to treat the tumor.

BACKGROUND OF THE INVENTION

Different types of apparatus have been used in the prior art for treating benign and cancerous tumors. For example, x-rays have been applied to a tumor to treat the tumor. Microwave energy has also been applied to a tumor to treat the tumor. Other forms of energy such as optical energy and laser energy have also been applied to a tumor to treat the tumor. The different types of apparatus used to treat tumors have been generally quite large and cumbersome.

The successful treatment of certain types of tumors is more difficult than the treatment of other types of tumors. For example, the successful treatment of brain tumors and other deep seated tumors, (malignant or benign) within a patient's body is more difficult than for superficial tumors. The objective of the treatment is to reduce in size or completely remove the tumor mass by one or more modalities available at the treatment facility. Common modalities are surgery, chemotherapy and x-ray therapy. A modality used alone or in conjunction with one of the above modalities is "tissue heating" or hyperthermia.

It is particularly well known that hyperthermia combined with x-ray therapy improves the complete response to a malignant tumor by a factor of two (2) compared to x-ray therapy alone. Hyperthermia is also known to have a greater effect on benign tumors compared to radiation therapy. Invasive microwave hyperthermia needles have long been known to be successful in treating brain tumors. With hyperthermia, a controlled thermal dose distribution is required for effective treatment of a deep-seated tumor.

Typical localized hyperthermia temperatures normally used for therapeutic treatment of cancer are in the approximately 42.5°C–45° C. range. This treatment is generally maintained for approximately thirty (30) minutes to sixty (60) minutes. Normal tissue should be maintained below temperatures of 42.5° C.

Ideally, a focussed radiation beam is concentrated at the tumor with minimal energy delivered to the normal tissue surrounding the tumor. Since the hyperthermia antenna beam width is proportional to the electric field wavelength, a small focal region suggests that the radiating wavelength be as small as possible. However, because of propagation losses in tissue, the depth of penetration of electromagnetic waves decreases with increasing transmittal frequency. For example, a radiating frequency of 915 MHz is used for non-invasive treatment of tumors to a depth of about three centimeters (3 cm) beneath the skin surface.

One of the significant problems in heating a tumor with a non-invasive hyperthermia antenna is the formation of undesired "hot spots" in surrounding tissue. This additional undesired heating often produces pain, burns and blistering in a patient. This sometimes requires termination of the treatment. Similar difficulties of irradiating superficial tissue with non-invasive x-ray applicators are sometimes encountered during deep tumor treatments. Thus, apparatus for, and techniques of, administering hyperthermia directly to a deep tumor site with interstitial x-ray applicators are needed.

An "Interstitial X-ray Needle" is disclosed and claimed in U.S. Pat. No. 5,165,093 issued on Nov. 17, 1992, in the names of Robert B. Miller, John R. Smith and Carl A. Muehlenweq as joint inventors and assigned to The Titan Corporation of San Diego, Calif. The x-ray needle includes a tube open at one end to receive electrons and to concentrate the electrons into a beam. An element is disposed at the other end of the tube to convert the electrons to x-rays and to provide for the passage of the x-rays to a tumor in a patient. The converter closes the tube at the other end of the tube. Thus, a fluid such as water is able to pass through a second tube coaxial with the first tube and cool the converter.

The diameter of the tube holding the fluid may be approximately two (2) millimeters. Because of its small size, the needle is able to be inserted into the patient's body to a position adjacent the tumor. The x-ray needle has the capability of locally inducing hyperthermia as a result of the conductive heat generated by the process of converting the electrons in the beam to x-rays. However, heat conduction limits the diameter of the region of the hyperthermic treatment to about six tenths of a centimeter (0.6 cm). Many tumors have a diameter in the order of two centimeters (2.0 cm) to three centimeters (3 cm). Because of limitations in heat conductivity, an x-ray needle alone cannot generate heat in a sufficiently large volume to treat the tumor.

It is known in the prior art that heating patterns in the order of three centimeters (3 cm) can be achieved by using microwave interstitial needles which are preferably cooled as by air. Without any form of cooling, a microwave interstitial needle can heat no more than a region in a diameter of about six tenths of a centimeter (0.6 cm) of tissue safely. It is also known that an optimal reduction in tumor cell survival is provided by x-ray irradiation during hyperthermal treatments—in other words, by simultaneous x-ray and heat treatment. Invasive x-ray needles currently in use do not allow simultaneous irradiation of tumors with x-rays and microwaves.

BRIEF DESCRIPTION OF THE INVENTION

This invention provides apparatus for, and methods of, providing a simultaneous treatment of a tumor in a patient's body by x-rays and microwave energy. It will be appreciated that other forms of energy (e.g. lasers and/or optics) may be used instead of x-rays. It will also be appreciated that radio frequency (rf) energy may be used in place of microwave energy. Actually, as used in the specification and the claims, the term "microwave energy" is intended to include radio frequency energy.

This invention adds a capability of providing radiation from a coaxial microwave antenna to an interstitial x-ray needle which may be water cooled. The outer diameter of the microwave antenna may be approximately three millimeters (3 mm). The microwave antenna may be coaxial with, and external to, the x-ray needle, which may have a diameter of approximately two millimeters (2 mm). The microwave antenna can be enclosed by a closed-end plastic catheter coaxial with the microwave antenna and having a diameter between approximately 3.8 millimeters and 4 millimeters. As a result of the air cooling of the microwave antenna and the water cooling of the x-ray apparatus, the hyperthermia needle can invasively cure tumors with a diameter as great as approximately three centimeters (3 cm).

In one embodiment of the invention, electrons are concentrated (e.g. magnetically) in a beam within a first tube. A converter converts the electrons to x-rays for movement to a particular position (e.g. tumor) in a patient. A fluid (e.g. water) flowing past the converter through a second tube co-axial with the first tube cools the converter. Microwave energy passes in the first direction through a third tube co-axial with the first tube. The third tube is open at the end near the converter so that the microwave energy will pass to the particular position in the patient. A second fluid (e.g. air) passing through a fourth tube coaxial with the first tube cools the microwave energy. The second, third and fourth tubes may respectively have diameters of approximately 2, 3 and 4 millimeters.

The microwave energy may pass into the third tube from a fifth tube transverse to the third tube. The microwave energy impedance at the fifth tube input may be approximately 50 and the microwave energy impedance at the third tube input may be approximately 5 Ω. The fifth tube is constructed to match the 50 Ω and 5 Ω impedances. A first portion of the microwave energy introduced to the third tube flows in the first direction through the third tube coaxially with the electron beam. A second portion of the microwave energy flows to a short circuit in a direction opposite to the first direction for reflection by the short circuit. The reflected microwave is in phase in the third tube with the microwave energy flowing in the first direction.

DETAILED DESCRIPTION OF THE INVENTION

Figure 1:
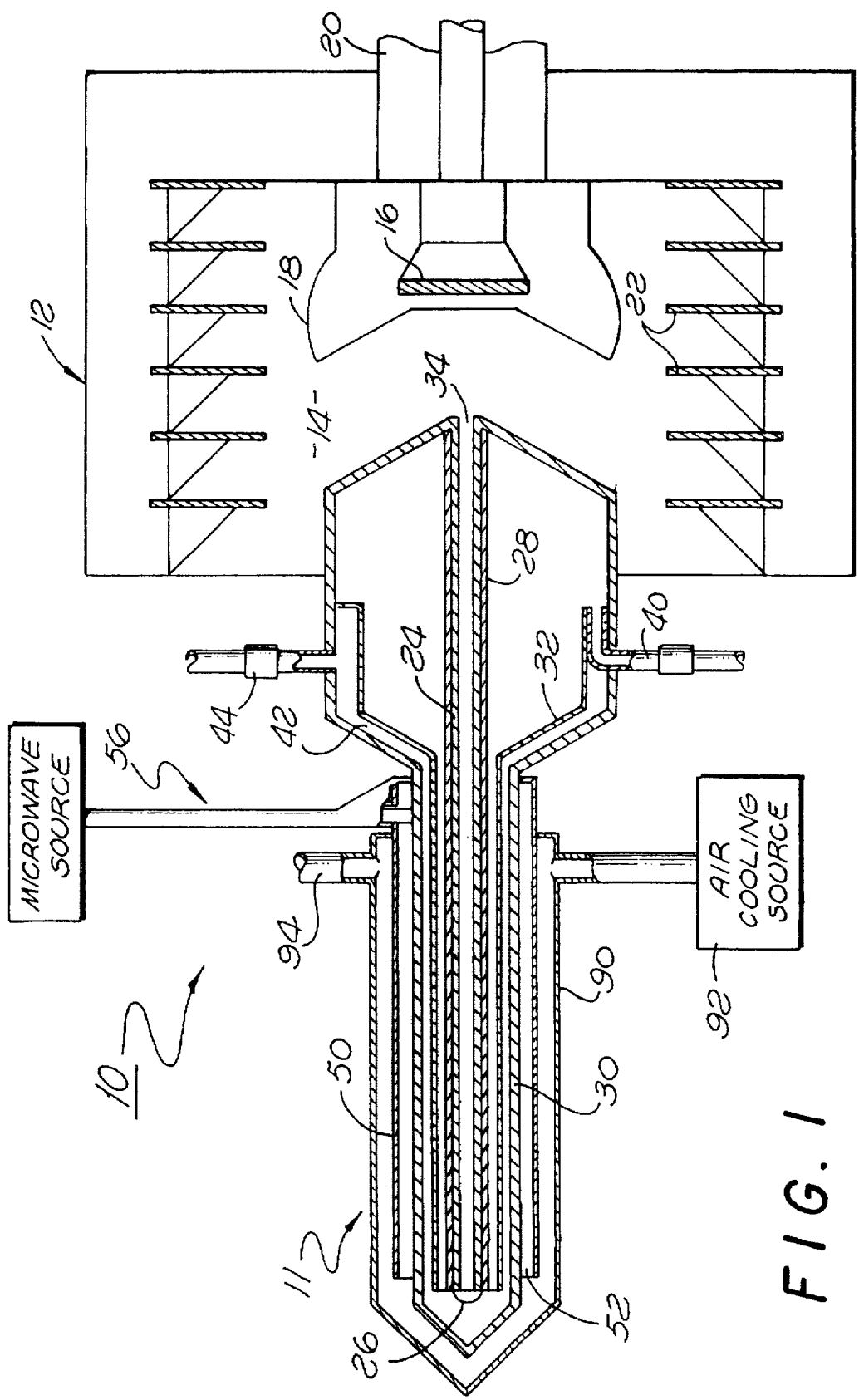
FIG. 1 is a Sectional view of apparatus including an X-ray needle and a microwave antenna enveloping the needle in a co-axial relationship with the needle.

As shown in FIG. 1, heat generating apparatus generally indicated at 10 includes a preferred embodiment of an X-ray needle generally indicated at 11. Such heat generating apparatus is shown and described in U.S. Pat. No. 5,164,093. The needle 11 is included within a housing 12. The housing 12 includes a vacuum chamber 14 which encloses an electron emitter 16 and a control grid 18. The electron emitter 16 is connected to a high voltage cable 20 which is in turn connected to a high voltage source (not shown). Insulators 22 are stacked between the electron emitter 16 and the housing 12.

The x-ray needle 11 includes an elongated tube 24 which is open at an end 34 within the vacuum chamber 14. The elongated tube 24 is connected at the other end to a converter element 26. The converter element 26 closes the other end of the tube 24. A solenoid coil 28 may be wound around the tube 24 along the length of the tube to focus the electrons into a beam during the movement of the electrons through the tube. It will be appreciated that other focussing means may be used in place of, or in addition to, the solenoid 28.

The electron beam can be confined to a diameter of approximately four tenths of a millimeter (0.4 mm) when the solenoid coil 28 provides a magnetic field of approximately 20 gauss. For a coil 28 having a resistance of approximately 13 ohms and wound at 20 turns per centimeter, the current in the coil is only about 0.8 amperes and the voltage across the coil is only about 0.1 volts. Thus, the power expended in the coil is only about 0.08 watts.

The electron beam is focussed by the solenoid coil 28 and is directed to the converter 26. The converter 26 is made from a material for converting the electron beams to x-rays which are directed to the tumor in the patient's body. These x-rays are effective in treating the tumor, partly by directing heat to the tumor. However, the heat generated by the x-rays has the ability to penetrate to a diameter of approximately only six tenths of a centimeter (0.6 cm). This may sometimes prevent the heat generated by the x-rays from treating the tumor since the tumor may have a diameter as great as approximately three centimeters (3 cm).

A casing 30 encloses the tube 24 and the solenoid coil 28 in a co-axial relationship with the tube. A pipe 32 is coaxially disposed between the tube 24 and the casing 30 to define a channel within the casing for the flow of water through a coolant inlet 40 and the channel to the converter element 26. The water then flows through a flow chamber 42 to a coolant outlet 44 in the casing 30. The water cools the converter element 26.

In one embodiment of the needle 11, the tube 24 may have an inside diameter of approximately 0.64 millimeters and an outside diameter of 0.81 millimeters. The solenoid coil 28 may be wound on the tube 24 with #33 magnet wire having a diameter of approximately 0.22 millimeter at approximately 40 turns per centimeter. The casing 30 may have an outside diameter of approximately 2.8 millimeters and an inside diameter of approximately 2.16 millimeters. The pipe 32 may have an inside diameter of approximately 1.52 millimeters and an outside diameter of approximately 1.83 millimeters. The water may flow through the pipe 32 at a flow rate of approximately 20 pounds per square inch. Thus, for an approximately 20 watt heat rate at the tip of the converter element 26, the increase in the temperature of the water over a period of ten (10) minutes is less than 5° C.

Figure 4:
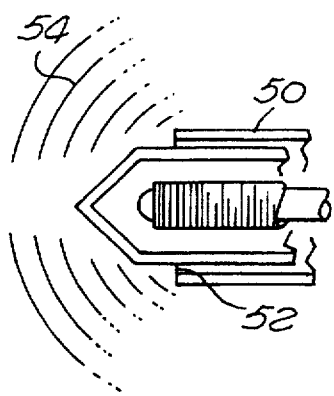
FIG. 4 schematically illustrates the pattern of the generation of the microwave energy.

A tube 50 is disposed on the tube 24 in co-axially displaced relationship with the tube. The tube 50 may have a diameter of approximately three millimeters (3 mm). As will be seen in detail from the subsequent discussion, microwave energy passes through the tube 50 to an open end 52 of the tube. The microwave energy is then directed from the open end 52 toward the tumor in the patient's body. The generation of the waves of the microwave energy is indicated schematically at 54 in FIG. 4. The microwave energy has the ability to penetrate the patient's body to diameters of approximately three (3) or four (4) centimeters. Thus, the microwave energy is effective in treating tumors with heat even when the tumors have diameters of approximately three (3) or four (4) centimeters.

Figure 3:
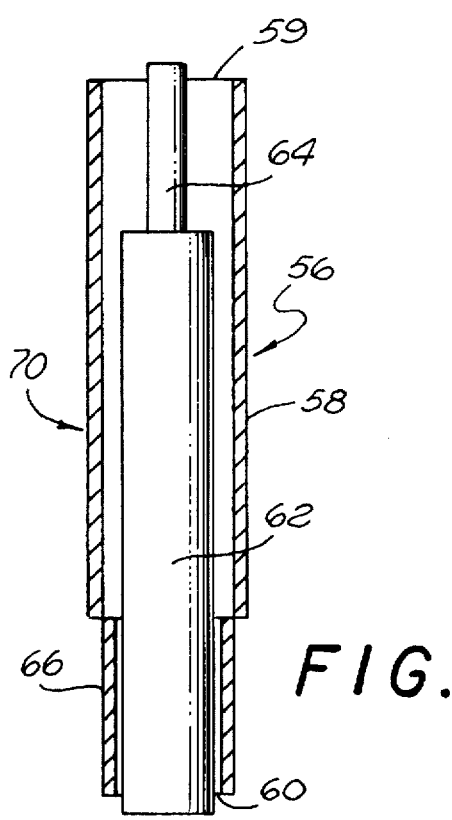
FIG. 3 is a sectional view of an input coaxial transmission line for introducing microwave energy to the microwave antenna shown in FIGS. 1, and the microwave antenna shown in FIG. 2, in a matched impedance relationship with the microwave antenna.

To introduce the microwave energy to the tube 50, a feedline generally indicated at 56 (FIGS. 1 and 3) may be provided. The feedline 56 may include a tube 58 (FIG. 3) made from a suitable material such as copper. The tube 58 may have an input end 59 and an output end 60. A solid rod 62 may be disposed in the tube 58 and may be made from a suitable material such as copper. The solid rod 62 may be relatively narrow at the input end 59 of the tube 58 to define a pin 64. In this way, a relatively great distance exists between the pin 64 and the tube 58 to define an impedance which matches the impedance of the equipment (not shown) supplying microwave energy to the feed line 56. This impedance may be approximately fifty ohms (50 Ω).

The input impedance to the tube 50 may be suitable value such as approximately five ohms (5 Ω). To provide a matching impedance in the feedline 56, a tube 66 with a reduced diameter relative to the tube 58 is provided in the feedline 56 at the end adjacent the tube 50. This causes the solid rod 62 to be disposed relatively close to the tube 66 at the output end of the feedline 56.

A section generally indicated at 70 is provided between the opposite ends of the feed line 56 to match the impedance of fifty ohms (50 Ω) at the input end of the feedline and the impedance of five ohms (5 Ω) at the output end of the feed line. This section may have a length of approximately one quarter of a wavelength. In this section, the distance between the rod 62 and the tube 58 is intermediate the distance between the pin 64 and the tube in the input section and the distance between the rod 62 and the tube 66 at the output end.

By providing the section 70 with a length of approximately one quarter of a wavelength (¼λ), the section 70 matches the impedance of approximately five ohms (5 Ω) at the output end of the feedline 56 to the impedance of fifty ohms (50 Ω) at the input end of the feedline. This may be seen from the following equation:

$$A=\sqrt{BC} \text{ where} \quad (1)$$

A=the impedance in the section 70;

B=the impedance of the feedline 56 at the input end of the feedline;

C=the impedance of the feedline 56 at the output end of the feed line;

Thus, $$A=\sqrt{(5)\times 50}=15.8 \ \Omega \quad (2)$$

The section 70 with a length of one quarter of a wave length and with the intermediate spacing between the tube 58 and the rod 62 accordingly provides an impedance of approximately 15.8.

The microwave wavelength in a dielectrically loaded coaxial cable is calculated from $$\lambda=\lambda_o\sqrt{\epsilon_r}, \text{ where} \quad (3)$$

$\epsilon_r$ is the relative dielectric constant and $\lambda_o=3.8\times10^{10}/f$ is the free space wavelength (the wavelength of the section 70 in FIG. 3) in centimeters. In the above equation, f=frequency. At a frequency of 915 MHz, the wavelength in a Teflon-filled metallic coaxial cable (the feedline 56) is calculated to be approximately 23.1838 centimeters. Thus, the section 70 will have a length (a quarter of a wavelength) of approximately 5.7959 centimeters. The length of each of the 50-ohm and 5-ohm sections respectively at the input and output ends of the feedline 56 will be approximately 2.5 centimeters.

The characteristic impedance of a coaxial transmission line is calculated from the equation $$Z_o=(138/\sqrt{\epsilon_r})\log_{10}(b/a), \text{ where} \quad (4)$$

a and b are the inner and outer radii of the coaxial transmission line. As previously described, copper material is used between the rod 62 and the pin 64 in the coaxial transmission line. The relative dielectric constant of Teflon is approximately 2.0 at microwave frequencies such as approximately 915 and 2450 MegaHertz. For the coaxial line 50 shown in FIG. 1, the inner radius "a" is approximately 1.054 millimeters (1.054 mm) and the outer radius "b" is approximately 1.201 millimeters (1.201 mm). As previously described, these values produce a characteristic impedance of approximately five ohms (5 Ω) at the input to the tube 50.

For a given value of inner conductor radius a in the feedline 56, it is possible to calculate the outer conductor radius b by solving equation (4) as $$b=a10(\sqrt{\epsilon_r}Z_o/138), \text{ where} \quad (5)$$

The value of $Z_o$ is obtained from equation (4). In the 5-ohm and 15.8 ohm sections, a=0.1054 centimeters and, in the 50 ohm section, a=0.0457 centimeters.

The coaxial microwave antenna attachment for the interstitial x-ray needle 11 can be operated at a microwave power level in the range of approximately 1 to 20 watts to generate therapeutic hyperthermic temperatures in tissue. The preferred microwave radiation frequencies are approximately 915 megahertz and 2450 megahertz. Radiation at 915 megahertz has a slightly greater penetration depth (by about 0.4 centimeters) in muscle tissue compared to radiation at 2450 MHz.

Figure 5:
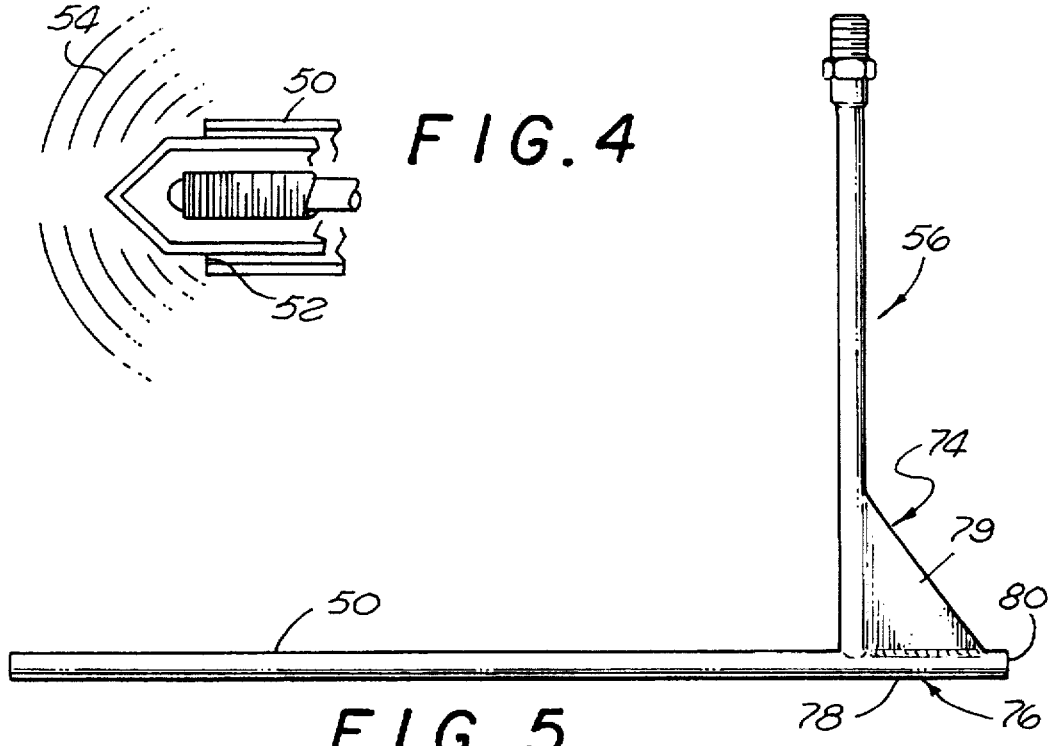
FIG. 5 schematically shows how the input coaxial line of FIG. 3 is combined mechanically with the apparatus shown in FIG. 1.

The coaxial feedline 56 is connected to the tube 50 by a microwave coaxial T- connection generally indicated at 74 (FIG. 5). The microwave coaxial T- connection 74 has one input signal path provided by the feedline 56 and has two (2) output signal paths. One of these output signal paths is provided by the tube 50. The other output signal path is provided by a short circuited path generally indicated at 76.

The short circuited path 76 is coaxial with the tube 50 but extends in a direction opposite to the direction of the tube. The short-circuited path 76 includes a coaxial transmission line 78 preferably having a length of approximately one quarter of a wave length. The outer diameter of the outer conductor of the line 78 is approximately 3 centimeters. The transmission line 78 is terminated by a short circuit 80.

In this way, a portion of the microwave energy from the feedline 56 is transmitted in FIG. 5 to the left in the direction of the tube 50. The other portion of the microwave energy from the feedline 56 is transferred to the short circuited path 76 for movement along the coaxial transmission line 78. Because of its length, the coaxial transmission line 78 changes the phase of the microwave energy by 90°. The phase of the microwave energy is further changed by 180° when it is reflected by the short circuit 80. The phase of the reflected microwave energy is again changed by 90° during its movement through the coaxial transmission line 78 toward the left after reflection by the short circuit 80. In this way, the portion of the microwave energy passing through the coaxial transmission line 78 into the tube 50 is in phase with the portion of the microwave energy passing directly into the tube 50.

The proper phase relationship discussed above for the coaxial transmission line 78 may be maintained by providing a right angle brace 79 on the feedline 56 and by attaching this brace as by solder to the coaxial transmission line 78. In this way, the feedline 56 is maintained rigidly in a right angle relationship with the coaxial transmission line 78.

The coaxial length of the needle 11 may vary from approximately ten centimeters (10 cm) to approximately twenty centimeters (20 cm) depending upon the depth of the tumor to be treated. The microwave attenuation α in a coaxial cable expressed in decibels per meter is $$\alpha_{dB}=8.686\times1.14\times10^{-6}\sqrt{\epsilon_r/\sigma}(1/a+1/b)(\log_{10}(b/a)) \quad (6)$$

where f is the microwave frequency and σ sigma is the electrical conductivity. For a needle length of approximately ten (10) to twenty (20) centimeters, copper (σ=5.7×10μ⁷) is the preferred coaxial conductor in order to minimize the microwave loss.

For a copper coaxial cable with an inner diameter of approximately two millimeters (2 mm) and an outer diameter of approximately three millimeters (3 mm), the microwave loss as computed from equation (6) is approximately 0.2 dB in ten centimeters (10 cm) of length. In clinical use, needles are often made of stainless steel. Stainless steel by itself may have too low of an electrical conductivity ($\sigma=2.0\times 10^6$) for practical use in the needle 11. However, the outer surface of the copper coaxial cable 50 can be coated with stainless steel without affecting the microwave loss.

A tube 90 (FIG. 1) may be disposed on the tube 50 to provide a path for the flow of air to cool the microwave energy flowing through the tube 50. The tube 90 may be provided with a suitable diameter such as approximately four millimeters (4 mm). The air may be provided from a source 92 and may be passed into the atmosphere through an outlet 94. The air flow through the tube 90 maintains the microwave energy radiated from the tube 50 at a suitable temperature such as approximately 41° C. In this way, a patient receiving the microwave energy for the treatment of a tumor cannot be burned in the areas around the tumor.

Figure 2:
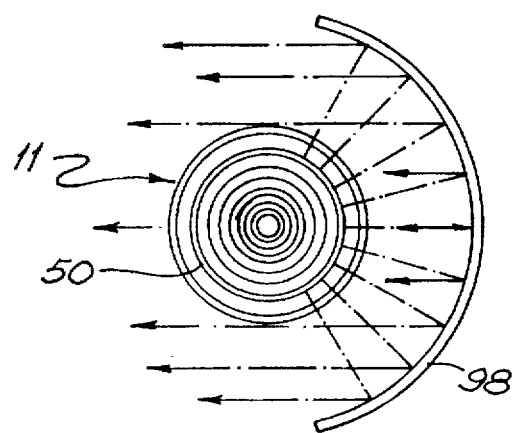
FIG. 2 is a sectional view taken substantially on the line 2—2 of FIG. 1 and shows another embodiment of the apparatus.

FIG. 2 illustrates another embodiment of the invention. This embodiment is similar to the embodiment shown in FIGS. 1 and 3–5 except that it includes a reflector 98 for reflecting the microwave energy to the particular position (e.g. the tumor) in the patient's body.

Although this invention has been disclosed and illustrated with reference to particular embodiments, the principles involved are susceptible for use in numerous other embodiments which will be apparent to persons of ordinary skill in the art. The invention is, therefore, to be limited only as indicated by the scope of the appended claims.

I claim:

1. In combinations for treating a patient, first means for generating electrons, second means for concentrating the electrons in an axial beam, third means for converting the electrons to x-rays and for directing the x-rays to a particular position in the patient's body, fourth means for providing microwave energy, fifth means for directing the microwave energy co-axially with the direction of the electron beam and for radiating the microwave energy to the particular position in the patient's body.

2. In a combination as set forth in claim 1, sixth means for cooling the third means, and seventh means for cooling the fifth means.

3. In a combination as set forth in claim 1, sixth means for providing a water cooling of the third means, and seventh means for providing an air cooling of the fifth means.

4. In a combination as set forth in claim 1 wherein the fourth means provides the microwave energy in a direction transverse to the direction of the axial beam of the electrons and wherein the fifth means directs the microwave energy in the axial direction.

5. In a combination as set forth in claim 1 wherein the second means is disposed in co-axial relationship with the third means at a position radially exterior to the third means and wherein the fifth means is disposed in co-axial relationship with the third means at a position radially exterior to the third means.

6. In a combination as set forth in claim 5 wherein sixth means is provided for cooling the third means and is disposed radially at a position between the third means and the fifth means and wherein seventh means is provided for cooling the fifth means and is disposed radially of the fifth means.

7. In a combination as set forth in claim 6 wherein the sixth means is disposed in co-axial relationship with the third means for water cooling the third means and wherein the seventh means is disposed in co-axial relationship with the fifth means for air cooling the fifth means.

8. In a combination as set forth in claim 1, the third means having a first impedance, the fifth means having a second impedance different from the first impedance, the fourth means being constructed to provide a match between the first and second impedances.

9. In an interstitial needle for directing energy to a patient's body, first means for directing electrons in a particular axial direction, a target disposed at one end of the first means and responsive to the electrons for producing x-rays and for directing the x-rays to a particular position in the patient's body, second means disposed in a co-axial relationship with the first means for directing a fluid past the target to cool the target, and third means disposed in a co-axial relationship with the first and second means for providing a second form of energy different from x-ray energy and for directing the energy in such second form to the particular position of the patient's body to heat the patient's body at such particular position.

10. In an interstitial needle as set forth in claim 9, the fluid constituting a first fluid, the second means being closed at the one end, fourth means disposed in a coaxial relationship with the first, second and third means for defining a closure with the second means at the one end, and fifth means for directing a second fluid through the closure defined by the second and fourth means to cool the energy directed through the second means.

11. In an interstitial needle as set forth in claim 9, the second means having properties of heating a greater area around the particular position in the patient's body than the area heated around such particular position by the x-rays.

12. In an interstitial needle as set forth in claim 9 wherein the third means provides microwave energy at a particular frequency to heat the patient's body in the area around such particular position.

13. In an interstitial needle as set forth in claim 9, the target closing the first means at the one end of the first means, the third means being open at the one end to direct the energy in the second form to the particular position of the patient's body to heat the patient's body at such particular position.

14. In an interstitial needle as set forth in claim 13 wherein the fluid constituting a first fluid, the second means being closed at the one end, fourth means disposed in a coaxial relationship with the first, second and third means for defining a closure with the second means at the one end, and fifth means for directing a second fluid through the closure defined by the second and fourth means to cool the energy directed through the second means, the second means having properties of heating a greater area around the particular position in the patient's body than the area heated around such particular position by the x-rays, the third means providing microwave energy at a particular frequency to heat the patient's body in the area around such particular position.

15. In a method of treating a patient, the steps of:

directing electrons in a particular axial direction, converting the electrons to x-rays at a particular position in the axial direction for the passage of the x-rays to a particular position in the patient's body, providing microwave energy, directing the microwave energy in a direction co-axial with the particular axial direction, and providing for the passage of the microwave energy to the particular position in the patient's body.

16. In a method as set forth in claim 15, the step of:

providing a converter at the position of conversion of the electrons to x-rays.

17. In a method as set forth in claim 15 wherein the microwave energy is provided at a selective one of approximately 915 and 2450 megahertz (MHz).

18. In a method as set forth in claim 15, the steps of:

cooling the converter, and cooling the path where the microwave energy is directed in the particular direction to the patient.

19. In a method as set forth in claim 15, the steps of:

directing water in a closed path past the converter in a direction co-axial with the particular axial direction to cool the converter, and directing air in a closed path past the position of the passage of the microwave energy to the particular position in the patient's body to cool the energy passing to the patient's body.

20. In a method as set forth in claim 19, the steps of:

providing a converter at the position of conversion of the electrons to x-rays, and providing the microwave energy at a selective one of frequencies of approximately 915 and 2450 megahertz (MHz).

21. In combination for treating a patient, first means for producing electrons, second means for directing the electrons in a particular axial direction, a converter for converting the electrons to x-rays and for passing the x-rays to a particular position in the patient's body, third means for providing microwave energy at a particular frequency, fourth means for providing for the passage of the microwave energy to the second means in a direction transverse to the particular axial energy, fifth means for providing for the passage of the microwave energy toward the converter in a direction co-axial with the direction of the electrons in the particular axial direction to obtain the passage of the microwave energy to the particular position in the patient's body.

22. In a combination as set forth in claim 21, sixth means for directing a first fluid in a closed path co-axial with the particular axial direction past the converter to cool the converter, and seventh means for directing a second fluid in a closed path co-axial with the particular axial direction to cool the microwave energy.

23. In a combination as set forth in claim 21, the fifth means including sixth means for directing a first portion of the microwave energy in the direction co-axial with the direction of the electrons in the particular axial direction and for directing a second portion of the microwave energy in an opposite direction co-axial with the direction of the electrons in the particular axial direction and for then reflecting the second portion of the microwave energy to move, in phase with the first portion of the microwave energy, in the same direction as of the first portion of the the microwave energy.

24. In a combination as set forth in claim 23, sixth means for directing a first fluid in a closed path co-axial with the particular axial direction past the converter to cool the converter, and seventh means for directing a second fluid in a closed path co-axial with the particular axial direction to cool the microwave energy, the third means having a first impedance, the fifth means having a second impedance different from the first impedance, the fourth means being constructed to provide a match between the first and second impedances.

25. In a method of treating a patient, the steps of:

directing electrons in a first axial direction to a first position, converting the electrons to x-rays at the first position for passage of the x-rays to a particular position in the patient's body, providing microwave energy, directing the microwave energy in the first axial direction in co-axial relationship with the movement of the electrons, and providing for the passage of the microwave energy to the particular position in the patient's body.

* * * * *